United States Patent [19]

Giobbio et al.

[11] Patent Number: 4,526,985

[45] Date of Patent: Jul. 2, 1985

[54] PROCESS FOR THE PREPARATION OF THE ANHYDRIDE OF N-FORMYL-L-ASPARTIC ACID

[75] Inventors: Vincenzo Giobbio, Turin; Giorgio Ornato; Livio Buracchi, both of Ivrea; Alberto Mangia, Milan, all of Italy

[73] Assignee: Pierrel S.p.A., Napoli, Italy

[21] Appl. No.: 514,585

[22] Filed: Jul. 18, 1983

[30] Foreign Application Priority Data

Aug. 6, 1982 [IT] Italy ................................ 22763 A/82

[51] Int. Cl.³ .......................................... C07D 307/66
[52] U.S. Cl. ..................................................... 549/253
[58] Field of Search ......................................... 549/253

[56] References Cited

FOREIGN PATENT DOCUMENTS 51-91210  8/1976  Japan .

OTHER PUBLICATIONS

Stevens et al., Recueil Trax. Chim., 83 (8), pp. 863–872, (1964).
Org. Syntheses, vol. 50, pp. 1–3.
Huffman, J. Org. Chem. 23, pp. 727–729 (1958).
Reese et al., J. C. S. Perkin I, pp. 934–939, (1975).

Primary Examiner—Henry R. Jiles
Assistant Examiner—Bernard I. Dentz
Attorney, Agent, or Firm—Bucknam and Archer

[57] ABSTRACT

A process for the preparation of the anhydride of N-formyl-L-aspartic acid by reacting L-aspartic acid with nearly stoichiometric amounts of formic acid and acetic anhydride, under controlled conditions of temperature, reaction and addition times. The product is a known intermediate in the synthesis of α-L-aspartyl-L-phenylalanine methyl ester, a known sweetening agent.

1 Claim, No Drawings

PROCESS FOR THE PREPARATION OF THE ANHYDRIDE OF N-FORMYL-L-ASPARTIC ACID

The present invention relates to a new process for the preparation of the anhydride of the N-formyl-L-aspartic acid, useful compound for the use in the peptide synthesis and particularly for the preparation of α-L-aspartyl-L-phenylalanine methylester, a known sweetening agent, whose synthesis was described in the Italian application No. 21674/78.

The methods up to now known for the preparation of the anhydride of N-formyl-L-aspartic acid rely on the reaction of formic acid and acetic anhydride with L-aspartic acid in experimental conditions different in molar ratios among the reagents, the solvents and the temperature and time conditions.

All the methods up to now known are however strongly limited in their industrial applicability either by the use of high excess of acetic anhydride and formic acid or by the use of aromatic and/or halo hydrocarbons, as described in the Japanese application Japan Kokai No. 76 91210 (Ajinomoto). Conspicuous problems from the economical, environmental and safety point of view derive, such as for instance difficulties in the treatment of residual mother-liquors, sudden and violent generation of carbon monoxide following side-reaction between formic acid and acetic anhydride, and a sudden exothermia, very difficult to control.

The process according to the present invention, on the contrary, allows to obtain, in excellent yields, the anhydride of N-formyl-L-aspartic-acid in high purity using nearly stoichiometric amounts of acetic anhydride and formic acid, the absence of solvents, and avoiding the above mentioned drawbacks.

In fact, it has been found that, with a ratio of 2.1 moles of acetic anhydride and 1.1 moles of formic acid per mole of aspartic acid, it is possible to obtain the anhydride of the N-formyl-aspartic acid with an assay higher than 95% and with a yield higher than 85%.

The process described in the already mentioned Japanese application, although limits the acetic anhydride to the stoichiometric, requires yet a molar ratio formic acid/aspartic acid at least 2/1, in addition to the use of aromatic and/or halo hydrocarbons for the isolation of the final product.

The reaction conditions according to the process of the present invention are characterized by a slow addition, during a 4–8 hours interval, of formic acid to the mixture of acetic anhydride and aspartic acid, at a temperature lower than 35° C. The resulting mixture is then allowed to react for at least 48 hours. The slow addition of the formic acid prevents the danger of heat accumulation, particularly serious in the case of industrial production, and, thanks to the maintenance of a temperature lower than 35° C., the generation of carbon monoxide, known side reaction of the formic acid in the presence of dehydrating agents such as acetic andhydride, is minimized (Rec. Trav. Chim. 83 (8), 863-72 (1964); J.C.S. Perkin I, (10), 934-42, (1975); Org. Synth. 50, 1-3; (1970); J. Org. Chem. 23, 727 (1958); Chem. Rev. 673, (1969)). The final product is isolated by simple cooling of the reaction mixture and filtration. The residual mother liquors are almost exclusively constituted by acetic acid, with traces of formic acid, and are therefore easily recovered.

The process according to the invention is therefore considerably more economical, easier and safer than the previously known methods.

The following examples illustrate the invention further on, without limiting, however, its scope.

EXAMPLE 1

133.2 G (1 mole) of L-aspartic acid are mixed with 214.2 g (2.1 moles) of acetic anhydride in a reaction flask. The mixture is heated up to 35° C. and, at this temperature, 50.6 g of formic acid (1.1 moles) are slowly added therein, during 5 hours. The reaction mixture is maintained under slow stirring always at the temperature of 35° C. for 48 more hours and finally cooled to 10°–12° C.

The solid obtained is filtered, and dried to give 128.8 g of a product, with an assay of 96.33% (titration with morpholine); $[\alpha]_D 20°$ -54.66. Solubility in acetone: complete.

The theoretical yield is 143 g; the reaction yield is therefore 86.76%.

The mother liquors from the filtration (260 ml) are constituted by a solution of derivative of aspartic acid in acetic acid, and containing only traces of formic acid.

EXAMPLE 2

33.3 G of aspartic acid (0.25 moles) are mixed with 53.55 g of acetic anhydride (0.525 moles); the mixture, under stirring, is then heated to 32° C. 12.65 G of formic acid (0.275 moles) are then slowly added during 5 hours.

Always under stirring, the temperature is kept at 30°–32° C. for 60 more hours. After cooling to 10° C. 31.92 g crystals having an assay of 95% are filtered under reduced pressure. The reaction yield is 85%.

EXAMPLE 3

13.3 Kg of aspartic acid are mixed in a glass reaction flask with 21.5 kg of acetic anhydride. The reaction mixture is heated up to 35° C., and, under stirring, 5 kg of formic acid are slowly added during 6 hours.

The reaction mixture is maintained under stirring at 35° C. for 48 more hours and is then cooled to 10° C.

12.2 Kg of the anhydride of N-formyl-L-aspartic acid having an assay of 97% are centrifuged. The reaction yield is 85.3%.

We claim:

1. A process for the preparation of the anhydride of N-formyl-L-aspartic acid which consists of adding slowly, during a period of 5–8 hours, formic acid to the mixture of L-aspartic acid and acetic anhydride, in the respective amounts of 2.00–2.10 moles of acetic anhydride and 1.00–1.10 moles of formic acid per mole of aspartic acid at a temperature of up to 35° C., in the absence of a solvent, letting the reaction mixture stand for a period of 48–60 hours and isolating said anhydride of N-formyl-L-aspartic acid from the reaction mixture.

* * * * *